(12) United States Patent
Sathe et al.

(10) Patent No.: US 10,919,855 B2
(45) Date of Patent: Feb. 16, 2021

(54) PROCESS TO PREPARE N-[2-[(1S)-1-(3-ETHOXY-4-METHOXY-PHENYL)-2-(METHYLSULPHONYL) ETHYL]-1,3-DIOXO-2,3-DIHYDRO-1H-ISOINDOL-4YL]ACETAMIDE

(71) Applicant: UNICHEM LABORATORIES LTD, Maharashtra (IN)

(72) Inventors: Dhananjay G. Sathe, Maharashtra (IN); Arijit Das, Goa (IN); Bhavesh B. Patel, Gujarat (IN); Dipak Subhash Patil, Maharashtra (IN); Ashok Govind Matale, Maharashtra (IN); Eknath Kamalakar Kshirsagar, Maharashtra (IN)

(73) Assignee: UNICHEM LABORATORIES LTD, Maharashtra (IN)

( * ) Notice: Subject to any disclaimer, the term of this patent is extended or adjusted under 35 U.S.C. 154(b) by 0 days.

(21) Appl. No.: 16/609,232

(22) PCT Filed: Apr. 27, 2018

(86) PCT No.: PCT/IB2018/052924
§ 371 (c)(1),
(2) Date: Oct. 29, 2019

(87) PCT Pub. No.: WO2018/203192
PCT Pub. Date: Nov. 8, 2018

(65) Prior Publication Data
US 2020/0181085 A1  Jun. 11, 2020

(30) Foreign Application Priority Data
May 4, 2017  (IN) .............................. 201721015701

(51) Int. Cl.
C07D 209/48  (2006.01)

(52) U.S. Cl.
CPC .................................. *C07D 209/48* (2013.01)

(58) Field of Classification Search
CPC ..................................................... C07D 209/48
See application file for complete search history.

(56) References Cited

U.S. PATENT DOCUMENTS 8,093,283 B2 * 1/2012 Muller .................... A61P 17/06
514/411

FOREIGN PATENT DOCUMENTS

WO    WO-2016199031 A1 * 12/2016 ........... C07C 317/28

OTHER PUBLICATIONS

Dyson et al. "Solvent effects in catalysis: rational improvements of catalysts via manipulation of solvent interactions" Catal. Sci. Technol., 2016, 6, 3302-3316 (Year: 2016).*

* cited by examiner

*Primary Examiner* — Joseph R Kosack
(74) *Attorney, Agent, or Firm* — Dickinson Wright PLLC

(57) ABSTRACT

An alternative and improved process for the preparation of Apremilast (Formula I) and Apremilast form B or a pharmaceutically acceptable salt thereof is provided. The novel process includes hydrogenation in acetone, Cyclization and acetylation followed by condensation in methyl isobutyl ketone (MIBK) and acetic acid mixture in specific volume ratios.

9 Claims, No Drawings

PROCESS TO PREPARE N-[2-[(1S)-1-(3-ETHOXY-4-METHOXY-PHENYL)-2-(METHYLSULPHONYL)ETHYL]-1, 3-DIOXO-2,3-DIHYDRO-1H-ISOINDOL-4YL]ACETAMIDE

This application claims the priority of Indian Application 201721015701 filed on May 4, 2017.

FIELD OF THE INVENTION

The present invention relates to an improved process for preparation of N-[2-[(1S)-1-(3-ethoxy-4-methoxyphenyl)-2-(methylsulphonyl) ethyl]-1, 3-dioxo-2,3-dihydro-1H-isoindol-4-yl]acetamide (Formula I).

BACKGROUND OF THE INVENTION

Formula I

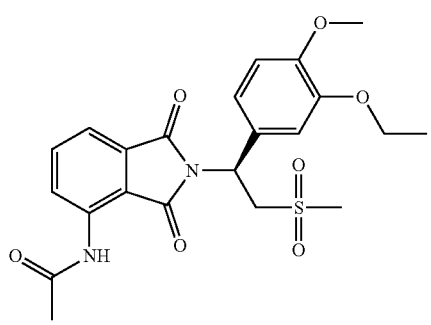

N-[2-[(1S)-1-(3-ethoxy-4-methoxyphenyl)-2-(methylsulphonyl) ethyl]-1, 3-dioxo-2,3-dihydro-1H-isoindol-4-yl]acetamide or 2-[1-(3-ethoxy-4-methoxy phenyl)-2-methylsulfonylethyl]-4-acetamidoisoindoline-1 ,3-dione or Apremilast (Formula I) was first claimed generically in U.S. Pat. No. 6,020,358. It is used in treatment of certain types of psoriasis and psoriatic arthritis. The drug acts as a selective inhibitor of the enzyme phosphodiesterase 4 (PDE4) and inhibits spontaneous production of TNF-alpha from human rheumatoid synovial cells.

Some process patents in prior describe routes of synthesizing Apremilast. EP1752148 (B1) discloses a process for the preparation of a racemic mixture of 2-[1-(3-ethoxy-4-methoxy phenyl)-2-methylsulfonylethyl]-4-acetamidoisoindoline-1 ,3-dione which comprises reacting 1-(3-ethoxy-4-methoxyphenyl)-2-methylsulfonylethyl amine with 3-acetamidophthalic anhydride in acetic acid at reflux for 15 hours. The drawback of this reaction is long reaction times and longer durations.

U.S. Pat. No. 8,455,536 B2 provides a process for the preparation of Apremilast, wherein the process involves the steps of:
a) reducing 3-nitrophthalic acid using 10% Pd/C in a Parr hydrogenator with $H_2$ up to 55 psi for 13 hours to obtain 3-aminopthalic acid;
b) reacting 3-aminopthalic acid with acetic anhydride at reflux temperature for 3 hours to obtain 3- acetamido phthalic anhydride;
c) resolution of racemic 2-(3-ethoxy-4-methoxyphenyl)-1-(methylsulphonyl)-eth-2-ylamine using N-acetyl-L-leucine in methanol at reflux for 1 hour to obtain (S)-2-(3-ethoxy-4-methoxy phenyl)-1-(methylsulphonyl)-eth-2-yl amine N-acetyl-L-leucine salt;
d) reacting overnight the N-acetyl-L-leucine salt of (S)-2-(3-ethoxy-4-methoxyphenyl)-1 -(methylsulphonyl)-eth-2-yl amine with 3-acetamidophthalic anhydride in 10 volume glacial acetic acid, at reflux temperature for 15 hours to obtain Apremilast.

The drawback of this reaction scheme is the longer duration required during the condensation and longer refluxing at higher temperatures.

CN 103864670 discloses the preparation of Apremilast by condensing 1-[(R)-amino(phenyl)methyl]-2-naphthol with 3-ethoxy-4-methoxybenzaldehyde in the presence of triethyl amine in methanol to yield the naphtho[1 ,2-e][1 ,3]oxazine derivative, which upon addition of dimethylsulfone lithium salt in tetrahydrofuran gives N-[(2S)-(1-(3-ethyoxyl-4-methoxyphenyl)-2-methylsulfonylethyl)]-(1R)-(a- aminobenzyl)-2-iso naphthol which undergoes hydrogenation over Pd/C in methanol to yield 1 (S)-(3-ethoxy-4-methoxyphenyl)-2-(methylsulfonyl)ethylamine, which is finally condensed with 3-acetamido phthalic anhydride in refluxing glacial acetic acid for 24 hours. The drawback of this scheme is longer duration of refluxing glacial acetic acid for 24 hours WO 20160189486 discloses the preparation of Apremilast by N-acetyl-L-leucine salt of (S)-2-(3-ethoxy-4-methoxyphenyl)-1-(methylsulphonyl)-eth-2-ylamine with 3-acetamidophthalic anhydride in glacial acetic acid, at reflux temperature for 11-12 hours followed by isolation and purification to obtain Apremilast. Higher reflux temperatures have to be maintained for longer durations and this is the drawback of this scheme.

The prior art processes disclosed above involve the condensation of N-acetyl-L-leucinesalt of chiral amine intermediate and 3-acetamidophthalic anhydride in acetic acid at reflux temperature. The condensation reaction takes more than 10-12 hours. The by-product of condensation reaction not removed from reaction media. There is formation of higher content of Des-acetyl impurity of Apremilast.

WO2017033116 provides a process for preparation of Apremilast wherein a non-carboxylic acid solvent is used for the condensation of L-pyroglutamate salt or N-acetyl-L-leucine salt of (S)-2-(3-ethoxy-4-methoxyphenyl)-1-(methylsulphonyl)eth-2-ylamine with 3-acetamidophthalic anhydride which provides Apremilast with less than 1% to 0.5% des-acetyl impurity w/w as determined by HPLC. The prior art processes disclosed the above condensation of N-acetyl-L-leucine or L-pyroglutamatesalt of chiral amine intermediate and reaction takes more than 1-12 hours.

There is a need to provide an alternative and improved process for the preparation of Apremilast (a compound of Formula I), and its crystalline Form B or a pharmaceutically acceptable salt thereof which has shorter durations, uses lower temperatures for reactions and yet produces Apremilast and its crystalline Form B of acceptable quality.

OBJECT OF THE INVENTION

The main object of the invention is to provide an alternative and improved process for the preparation of Apremilast (a compound of Formula I) or a pharmaceutically acceptable salt thereof.

Another object of the invention is to provide an alternative and improved process for the preparation of Apremilast Form B (a compound of formula I) or a pharmaceutically acceptable salt thereof.

Another object of the invention is to provide an improved process to prepare Apremilast and its crystalline Form B, which has shorter reaction times.

Yet another object of the invention is to provide an improved process of shorter reactions times to prepare Apremilast and its crystalline Form B having less than 0.15% w/w by HPLC of Des-acetyl impurity.

SUMMARY OF THE INVENTION:

Accordingly the invention provides an alternative and improved process for the preparation of Apremilast (a compound of Formula I) or a pharmaceutically acceptable salt thereof.

Another object of the invention is to provide an alternative and improved process for the preparation of Apremilast Form B (a compound of formula I) or a pharmaceutically acceptable salt thereof.

An improved process to prepare Apremilast and its crystalline Form B, as provided by this invention has shorter reaction times.

An improved process of shorter reactions times to prepare Apremilast and its crystalline Form B provided by this invention produces Apremilast and its crystalline Form B having less than 0.15% w/w by HPLC of Des-acetyl impurity.

There is provided an improved process of shorter reactions times for preparation of a pharmaceutically acceptable Apremilast Form B, having less than 0.15% w/w by HPLC of Des-acetyl impurity, comprising steps of
  i. Hydrogenation of 3-nitrobenzene-1, 2-dicarboxylic acid (Formula -II) in presence of 10% Palladium on carbon and acetone to prepare 3-aminobenzene-1, 2-dicarboxylic acid (Formula -III).
  ii. Cyclization and acetylation of 3-aminobenzene-1, 2-dicarboxylic acid (Formula -III) obtained in step i) is treated with acetic anhydride to prepare N-(1, 3-dioxo-1, 3dihyro-2-benzofuran-4-yl) acetamide (Formula-IV).
  iii. Condensation of (1S)-1-(3-ethoxy-4-methoxy-phenyl)-2-methanesulfonyl-ethyl amine (Formula-V) and N-(1, 3 -dioxo-1, 3dihyro-2-benzofuran-4-yl) acetamide (Formula-IV) in presence of methyl isobutyl ketone and acetic acid mixture of solvent to prepare N-[2-[(1S)-1-(3-ethoxy-4-methoxyphenyl)-2-(methylsulphonyl) ethyl]-1, 3-dioxo-2,3-dihydro-1H-isoindol-4-yl]acetamide (Formula-I).
  iv. Crystallization of N-[2-[(1S)-1-(3-ethoxy-4-methoxy-phenyl)-2-(methylsulphonyl) ethyl]-1, 3-dioxo-2,3-dihydro-1H-isoindol-4-yl]acetamide (Formula-I) prepared in step iii using suitable solvent to obtain Apremilast Form-B having less than 0.15% w/w by HPLC of Des-acetyl impurity.

The present invention further provides a process for preparation of Apremilast (Formula I) having less than 0.15% w/w by HPLC of Des-acetyl impurity, comprising steps of:
  i. hydrogenation of 3-nitrobenzene-1, 2-dicarboxylic acid (Formula -II) in presence of suitable catalyst and suitable solvent to prepare 3-aminobenzene-1, 2-dicarboxylic acid (Formula -III);
  ii. cyclization and acetylation of 3-aminobenzene-1, 2-dicarboxylic acid (Formula -III) obtained in step i) with acetic anhydride to prepare N-(1, 3-dioxo-1, 3dihyro-2-benzofuran-4-yl) acetamide (Formula-IV); and
  iii. condensation of (1S)-1-(3-ethoxy-4-methoxy-phenyl)-2-methanesulfonyl- ethylamine (Formula-V) and N-(1, 3-dioxo-1, 3dihyro-2-benzofuran-4-yl) acetamide (Formula-IV) in presence of methyl isobutyl ketone and acetic acid mixture to prepare Apremilast (Formula I) having less than 0.15% w/w by HPLC of Des-acetyl impurity.

The present invention provides a process for preparation of Apremilast (Formula I) wherein the process comprises condensation of (1S)-1-(3-ethoxy-4-methoxy-phenyl)-2-methanesulfonyl-ethylamine (Formula-V) and N-(1, 3-di-oxo-1, 3dihyro-2-benzofuran-4-yl) acetamide (Formula-IV) in presence of methyl isobutyl ketone and acetic acid mixture. The present invention provides a process for preparation of Apremilast (Formula I) wherein the process comprises condensation of (1S)-1-(3-ethoxy-4-methoxy-phenyl)-2-methanesulfonyl-ethylamine (Formula-V) and N-(1, 3-dioxo-1, 3dihyro-2-benzofuran-4-yl) acetamide (Formula-IV) in presence of methyl isobutyl ketone and acetic acid mixture, wherein the process comprises continuous removal of water formed during the condensation reaction by azeotropic distillation.

The present invention also provides a process of hydrogenation of 3-nitrobenzene-1, 2-dicarbxylic acid (Formula -II) to prepare 3-aminobenzene-1, 2-dicarboxylic acid (Formula -III) using Acetone as solvent at lower temperature.

The present invention further provides process of chiral purification or optical purification of (1S)-1-(3-ethoxy-4-methoxy-phenyl)-2-methanesulfonyl-ethylamine (Formula-V) in presence of suitable solvents at suitable temperature to prepare stereochemically pure (1S)-1-(3-ethoxy-4-methoxy-phenyl)-2-methanesulfonyl-ethylamine (Formula-V).

The present invention provides Apremilast (Formula I) having less than 0.15% w/w by HPLC of Des-acetyl impurity.

The present invention provides Apremilast Form B having less than 0.15% w/w by HPLC of Des-acetyl impurity.

DETAILED DESCRIPTION OF THE INVENTION

Accordingly there is provided an improved process of shorter reactions times for preparation of a pharmaceutically acceptable Apremilast Form-B, having less than 0.15% w/w by HPLC of Des-acetyl impurity, comprising steps of
  i. Hydrogenation of 3-nitrobenzene-1, 2-dicarboxylic acid (Formula -II) in presence of 10% Palladium on carbon and acetone to prepare 3-aminobenzene-1, 2-dicarboxylic acid (Formula -III).
  ii. Cyclization and acetylation of 3-aminobenzene-1, 2-dicarboxylic acid (Formula -III) obtained in step i) is treated with acetic anhydride to prepare N-(1, 3-dioxo-1, 3dihyro-2-benzofuran-4-yl) acetamide (Formula-IV).
  iii. Condensation of (1S)-1-(3-ethoxy-4-methoxy-phenyl)-2-methanesulfonyl-ethylamine (Formula- V) and N-(1, 3-dioxo-1, 3dihyro-2-benzofuran-4-yl) acetamide (Formula-IV) in presence of methyl isobutyl ketone and acetic acid mixture of solvent to prepare N-[2-[(1S)-1-(3-ethoxy-4-methoxyphenyl)-2-(methylsulphonyl) ethyl]-1, 3-dioxo-2,3-dihydro-1H-isoindol-4-yl]acetamide (Formula-I).
  iv. Crystallization of N-[2-[(1S)-1-(3-ethoxy-4-methoxy-phenyl)-2-(methylsulphonyl) ethyl]-1, 3-dioxo-2,3-dihydro-1H-isoindol-4-yl]acetamide (Formula-I) prepared in step iii using suitable solvent to obtain Apremilast Form-B having less than 0.15% w/w by HPLC of Des-acetyl impurity.

The present invention further provides a process for preparation of Apremilast (Formula I) having less than 0.15% w/w by HPLC of Des-acetyl impurity, comprising steps of:
  i. hydrogenation of 3-nitrobenzene-1, 2-dicarboxylic acid (Formula -II) in presence of suitable catalyst and suitable solvent to prepare 3-aminobenzene-1, 2-dicarboxylic acid (Formula -III);
  ii. cyclization and acetylation of 3-aminobenzene-1, 2-dicarboxylic acid (Formula -III) obtained in step i) with acetic anhydride to prepare N-(1, 3-dioxo-1, 3dihyro-2-benzofuran-4-yl) acetamide (Formula-IV); and
  iii. condensation of (1S)-1-(3-ethoxy-4-methoxy-phenyl)-2-methanesulfonyl-ethylamine (Formula-V) and N-(1, 3-dioxo-1, 3dihyro-2-benzofuran-4-yl) acetamide (Formula-IV) in presence of methyl isobutyl ketone and acetic acid mixture to prepare Apremilast (Formula I) having less than 0.15% w/w by HPLC of Des-acetyl impurity.

3-nitrobenzene-1, 2-dicarboxylic acid (Formula -II) is reduced in presence catalyst selected from 10% Palladium on carbon, Raney nickel or alike and in presence of suitable solvent selected from acetone, methanol, ethanol at temperature 15° C.-20° C. to prepare 3-aminobenzene-1, 2-dicarboxylic acid (Formula -III). The preferred solvent for the reaction is Acetone. The reaction is performed in the temperature range of 5° C. to 25° C. However in the range of 15° C. to 20° C. it works well.

Cyclization and acetylation of 3-aminobenzene-1, 2-dicarboxylic acid (Formula -III) is carried out in presence of acetic anhydride at temperature 130° C.-140° C. After completion of the reaction, reaction mass is filtered and washed with methyl tert. butyl ether to prepare N-(1, 3-dioxo-1, 3dihyro-2-benzofuran-4-yl) acetamide (Formula-IV). Optionally the reaction mass is cooled to 5° C., filtered and washed with methyl tert. butyl ether to prepare N-(1, 3-dioxo-1, 3-dihydro-2-benzofuran-4-yl) acetamide (Formula-IV). The reaction can also be performed in the temperature range of 90° C. to 140° C. However in the range of 130° C.-140° C. it works well.

Condensation of (1S)-1-(3-ethoxy-4-methoxy-phenyl)-2-methanesulfonyl-ethylamine (Formula-V) and N-(1, 3-dioxo-1, 3-dihydro-2-benzofuran-4-yl) acetamide (Formula-IV) is carried out in presence of methyl isobutyl ketone (MIBK) and acetic acid mixture at temperature 115° C.-120° C. and water formed during the reaction is removed by azeotropic distillation. Product is extracted in ethyl acetate and is isolated using acetone and ethanol to prepare N-[2-[(1S)-1-(3-ethoxy-4-methoxyphenyl)-2-(methylsulphonyl) ethyl]-1, 3 -dioxo-2,3 -dihydro-1H-isoindol-4-yl]acetamide (Formula-I), which is purified using acetone and ethanol to get Apremilast form-B.

The present invention provides a process for preparation of Apremilast (Formula I) wherein the process comprises condensation of (1S)-1-(3-ethoxy-4-methoxy-phenyl)-2-methanesulfonyl-ethylamine (Formula-V) and N-(1, 3-dioxo-1, 3dihyro-2-benzofuran-4-yl) acetamide (Formula-IV) in presence of methyl isobutyl ketone and acetic acid mixture.

The present invention further provides a process for preparation of Apremilast (Formula I) wherein the process comprises condensation of (1S)-1-(3-ethoxy-4-methoxy-phenyl)-2-methanesulfonyl-ethylamine (Formula-V) and N-(1, 3-dioxo-1, 3dihyro-2-benzofuran-4-yl) acetamide (Formula-IV) in presence of methyl isobutyl ketone and acetic acid mixture, wherein the process comprises continuous removal of water formed during the condensation reaction by azeotropic distillation.

During condensation water is produced as byproduct. Water causes hydrolysis of N-acetyl group and generates de-acetyl Apremilast as impurity. This impacts the quality of final product.

EP1752148 (B1) discloses a process for the preparation of a racemic mixture of 2-[1-(3-ethoxy-4- methoxy phenyl)-2-methylsulfonylethyl]-4-acetamidoisoindoline-1 ,3-dione which comprises reacting 1-(3-ethoxy-4-methoxyphenyl)-2-methylsulfonylethyl amine with 3-acetamidophthalic anhydride in acetic acid at reflux for 15 hours. This is considerably long reaction time. Surprisingly in presence of mixture of MIBK and acetic acid, the reaction is completed in very short period of about 30-60 min.

CN 103864670 describes the process in which similar step is carried out and it necessitates refluxing glacial acetic acid for 24 hours.

WO2017033116 provides a process for preparation of Apremilast wherein a non-carboxylic acid solvent is used for the condensation of L-pyroglutamate salt or N-acetyl-L-leucine salt of (S)-2-(3-ethoxy-4-methoxyphenyl)-1-(methylsulphonyl)eth-2-yl amine with 3-acetamidophthalic anhydride which provides Apremilast with less than 1% to 0.5% des-acetyl impurity w/w as determined by HPLC. The prior art processes disclosed the above condensation of N-acetyl-L-leucine or L-pyroglutamate salt of chiral amine intermediate and reaction takes more than 1-12 hours.

Although the claims of this patent claim use of base, nowhere the application describes and exemplifies use of the base. All examples are illustrated using salt and not base. The reaction is known to be acid catalyzed and therefore when salt is used, cation resulting from the salt used provides required acidity to allow the reaction to complete. Therefore presence of salt performs the same function as the presence of carboxylic acid solvent.

Solvents such as IPA, n-butanol or MIBK can be used either singularly or in combination with acetic acid. It is observed that although the reaction can be performed using n-butanol or IPA singularly, quality of the product is not acceptable. Use of plain acetic acid also results in the product with less purity. It was observed that use of plain MIBK in the condensation reaction does not complete the reaction besides generation of impurity. The novelty and the inventive step of the invention resides in use of mixture of MIBK and Acetic acid in certain proportion in condensation step. Use of binary mixture of MIBK (11V)/Acetic acid (4V) or MIBK (12V)/Acetic acid (4.4V) or MIBK (12V)/Acetic acid (4.5V) gives very good results.

Use of such mixture is not reported and is novel. It was surprisingly observed that when MIBK is used with Acetic acid in certain volume proportions, there is insignificant formation of des-acetyl Apremilast impurity. The quality of the product is acceptable as per ICH guidelines related to known impurity criteria.

It was also surprisingly observed that both reactants exhibit better solubility in presence of Acetic acid used in combination with MIBK. Surprisingly it was further observed that when binary mixture of solvents i.e. MIBK and acetic acid is used, condensation reaction completed in much shorter time of about an hour as compared to 12-15 hours (overnight) as described in U.S. Pat. No. 8,455,536 B2 process using Acetic acid for completion. The process described in U.S. Pat. No. 8,455,536 B2 necessitates reacting overnight the N-acetyl-L-leucine salt of (S)-2-(3-ethoxy-4-methoxyphenyl)-1-(methyl sulphonyl)-eth-2-yl amine with 3-acetamidophthalic anhydride in 10 volume glacial acetic acid, at reflux temperature for 15 hours to obtain Apremilast.

Surprisingly it was also observed that when mixture of MIBK and acetic acid is used in specific proportions in condensation, the reaction does not require lengthy refluxing at higher temperatures and there is no formation of Dimer impurity. Use of threshold volumes of MIBK:Acetic acid of critical importance. Use of volume ratios of 11-12:4-4.5 gives good results. When MIBK:Acetic acid is used in the volume ratio of 11:4 or 12:4.4 the reaction works well with no formation of dimer impurity. Use of lower volume ratios allows the reaction to work well but there is formation of dimer impurity jeopardizing quality of yield. If the volume ratios are maintained at 8:3 the reaction works but there is formation of dimer impurity. Use of specific proportions of volume ratios also gives good yields of Apremilast form B. Thus use of MIBK and acetic acid is used in specific proportions controls des-acetyl and dimer impurities.

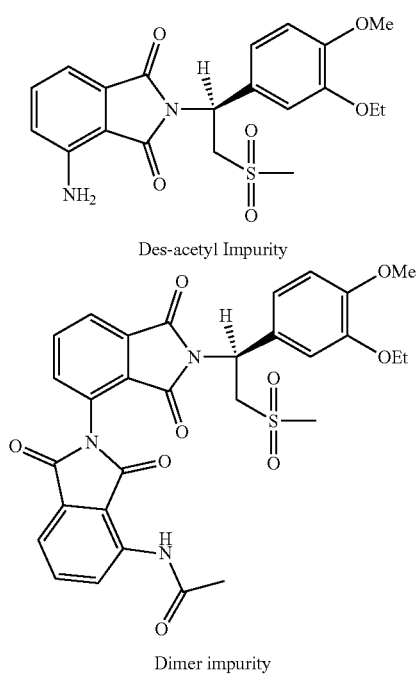

The improved process for the preparation of Apremilast form B provides less than 0.15% w/w by HPLC of Des-acetyl impurity and completes the condensation reaction within 30-60 min.

The reaction scheme for the synthesis of Apremilast is as follows:

Scheme-

1). Hydrogenation:

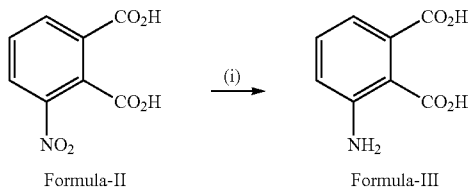

2). Cyclization and acetylation:

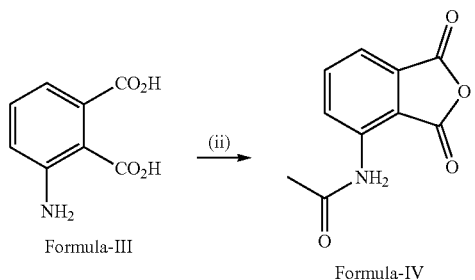

3). Condensation:

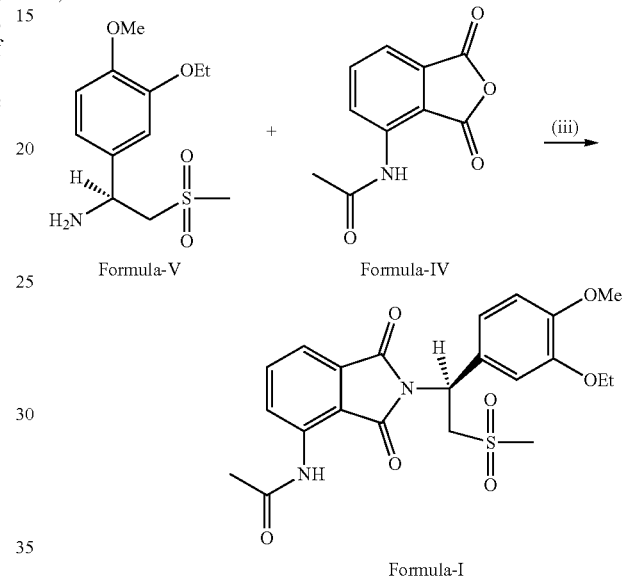

Reagent: (i) 10% Palladium on carbon, acetone, 15-20° C., 3 hr: (ii) Acetic anhydride, 130-140° C., 2 hr: (iii) MIBK, acetic acid, 115-120° C., 30-60 min.

Alternative and improved process for the preparation of Apremilast form B is to be understood as a one more process to produce Apremilast Form B which is free from defects associated with the prior art processes. It is also a process with shorter reaction times. It is a process to prepare Apremilast form B having less than 0.15% w/w by HPLC of Des-acetyl impurity.

Although hydrogenation and cyclization followed by acetylation per say are known, the whole process where these two steps are followed by condensation as depicted in this invention are not known.

The present invention also provides a process of hydrogenation of 3-nitrobenzene-1, 2-dicarboxylic acid (Formula -II) to prepare 3-aminobenzene-1, 2-dicarboxylic acid (Formula -III) using Acetone as solvent. Solvent used in the hydrogenation is novel for this reaction and has a surprising effect of reduction in reaction time and quality of hydrogenated product. The present invention further provides process of chiral purification or optical purification of (1S)-1-(3-ethoxy-4-methoxy-phenyl)-2-methanesulfonyl-ethylamine (Formula-V) in presence of suitable solvents at suitable temperature to prepare stereochemically pure (1S)-1-(3-ethoxy-4-methoxy-phenyl)-2-methanesulfonyl- ethyl-amine (Formula-V).

Chiral purification of (1S)-1-(3-ethoxy-4-methoxy-phenyl)-2-methanesulfonyl-ethylamine (Formula-V) is carried out in presence of ethyl acetate alone or optionally in presence of n-hexane at temperature 65-75° C., cooled to ambient temperature, filtered and washed with a mixture of n-hexane: ethyl acetate to prepare pure (1S)-1-(3-ethoxy-4-methoxy-phenyl)-2-methanesulfonyl-ethylamine (Formula-V).

Thus as described in the detailed description and illustrated by examples in example section, the objects of the invention are achieved. The invention provides an alternative and improved process for the preparation of Apremilast (a compound of formula I), Apremilast form B or a pharmaceutically acceptable salt thereof.

The invention has provided an improved process to prepare Apremilast and Apremilast form B, which has shorter reaction times.

The invention has provided an improved process of shorter reactions times to prepare Apremilast and Apremilast form B having less than 0.15% w/w by HPLC of Des-acetyl impurity.

The present invention further provides Apremilast (Formula I) having less than 0.15% w/w by HPLC of Des-acetyl impurity.

The present invention also provides Apremilast Form B having less than 0.15% w/w by HPLC of Des-acetyl impurity.

EXAMPLES

Example 1

Preparation of 3-Aminobenzene-1, 2-Dicarboxylic acid or 3-Amino Phthalic Acid (Formula-III)

3-Nitrobenzene-1,2-dicarboxylic acid or 3-Nitro Phthalic acid (Formula -II) (200 gm) and 10% Pd/C (10 gm) in acetone (2400 ml) charge in autoclave and maintain hydrogen pressure of 3-4 kg/cm$^2$ for 3 hr at 15-20° C. (15-25° C.) in autoclave. Filter reaction through hyflobed and distill out reaction mass completely. Charge ethyl acetate followed by n-hexane. Stir reaction mass for 2 hr at ambient temperature and filtered resulting Formula II with 95% yield and 94.98% HPLC purity.

The reaction works well when the quantity of 10% Pd/C used is 5 gm and hydrogenation is completed.

Example 2

Preparation of 3-Aminobenzene-1, 2-Dicarboxylic Acid or 3-Amino Phthalic Acid (Formula-III)

3-Nitrobenzene-1,2-dicarboxylic acid or 3-Nitro Phthalic acid (Formula -II) (50 gm) and 10% Pd/C (5 gm) in ethanol (500 ml) charge in autoclave and maintain hydrogen pressure of 3-4 kg/cm$^2$ for 1 hr at 15-20° C. (15-25° C.) in autoclave. Filter reaction through hyflobed and distill out reaction mass completely. Charge ethyl acetate followed by n-hexane. Stir reaction mass for 2 hr at ambient temperature and filtered resulting Formula II with 80% yield and 98.72% HPLC purity.

Example 3

Preparation of N-(1, 3-Dioxo-1, 3Dihyro-2-Benzofuran-4-Yl) Acetamide or 3-Acetamido-Phthalic Anhydride (Formula-IV)

3-Aminobenzene-1, 2-dicarboxylic acid or 3-Amino Phthalic acid (Formula-III) (150 gm) into acetic anhydride (525 ml) at 25-30° C. Raise temperature up to 130-140° C. and maintain 2 hr. After completion of reaction gradually cool to ambient temperature. Stir reaction mass for 2 hr and cool up to 0-5° C. (0-10° C.). Filter the product and wash with methyl tert. butyl ether resulting Formula IV with 78.6% yield and 99.49% HPLC purity.

Example 4

Chiral Purification of (1S)-1-(3-Ethoxy-4-Methoxy-Phenyl)-2-Methanesulfonyl-Ethylamine (Formula-V) by Crystallization Charge ethyl acetate (350 ml) and charge (1S)-1-(3-ethoxy-4-methoxy-phenyl)-2-methanesulfonyl-ethylamine (Formula-V) (100 gm) at temperature 65-75° C., cool up to ambient temperature, filtered and wash with n-hexane: ethyl acetate mixture of solvent to get pure (1S)-1-(3-ethoxy-4-methoxy-phenyl)-2-methanesulfonyl-ethylamine (Formula-V).

Example 5

Preparation of N-[2-[(1S)-1-(3-Ethoxy-4-Methoxy-phenyl)-2-(Methylsulphonyl) Ethyl]-1, 3-Dioxo-2, 3-Dihydro-1H-Isoindol-4-yl] Acetamide (Formula-I)

(1S)-1-(3-ethoxy-4-methoxy-phenyl)-2-methanesulfonyl-ethylamine (Formula-V) (125 gm) and N-(1, 3-dioxo-1, 3dihyro-2-benzofuran-4-yl) acetamide (Formula-IV) (98.5 gm) in to methyl isobutyl ketone (1500 ml) and acetic acid (550 ml) mixture of solvent at ambient temperature. Raise temperature up to 115-120° C. (115-125° C.). Remove the water formed during the reaction. After completion of reaction distill out reaction mass completely. Charge ethyl acetate for extraction and wash with sodium bicarbonate solution and sodium chloride solution. Distill out reaction mass completely and charge acetone followed by ethanol. Raise temperature up to reflux and maintain 1 hr. Reaction gradually cool to ambient temperature and maintain reaction mass and stir for 7-8 hr. Filter the product and wash with ethanol. Charge wet cake into acetone followed by ethanol. Raise temperature up to reflux and maintain 1 hr. Reaction gradually cool to ambient temperature and maintain reaction mass and stir for 7-8 hr. Filter the product and wash with ethanol resulting Formula I with 73.1% yield and 99.98% HPLC purity and 99.99 Chiral purity. The titled product having XRPD values as, 10.1, 12.4, 13.5, 20.8, 22.5, 24.7, and 27.0 ±0.2° (Form-B).

We claim:
1. A process to prepare Apremilast form B comprising steps of;
  i. hydrogenation of 3-nitrobenzene-1, 2-dicarboxylic acid (Formula-II) in presence of suitable reducing agent and acetone as a solvent at a suitable temperature to prepare 3-aminobenzene-1, 2-dicarboxylic acid (Formula-III);
  ii. cyclization and acetylation of 3-aminobenzene-1, 2-dicarboxylic acid (Formula-III) obtained in step i) with acetic anhydride at suitable temperature to prepare N-(1, 3-dioxo-1, 3-dihydro-2-benzofuran-4-yl) acetamide (Formula-IV);
  iii. condensation of (1S)-1-(3-ethoxy-4-methoxy-phenyl)-2-methanesulfonyl-ethylamine (Formula-V) and N-(1, 3-dioxo-1, 3-dihydro-2-benzofuran-4-yl) acetamide (Formula-IV) in presence of methyl isobutyl ketone (MIBK) and acetic acid mixture, wherein MIBK and acetic acid is in the ratio of 11:4 to 12:4.5 to prepare

N-[2-[(1S)-1-(3-ethoxy-4-methoxyphenyl)-2-(methylsulphonyl) ethyl]-1, 3-dioxo-2,3-dihydro-1H-isoindol4-yl]acetamide (Formula-I);

iv. crystallization of N-[2-[(1S)-1-(3-ethoxy-4-methoxyphenyl)-2-(methylsulphonyl) ethyl]-1, 3-dioxo-2,3-dihydro-1H-isoindol4-yl]acetamide (Formula-I) prepared in step iii using a suitable solvent to obtain Apremilast Form B.

2. A process for preparation of Apremilast (Formula I) having less than 0.15% w/w of Des-acetyl impurity, the process comprising steps of:

i. hydrogenation of 3-nitrobenzene-1, 2-dicarboxylic acid (Formula - II) in presence of suitable catalyst and acetone as a solvent to prepare 3-aminobenzene-1, 2-dicarboxylic acid (Formula -III);

ii. cyclization and acetylation of 3-aminobenzene-1, 2-dicarboxylic acid (Formula- III) obtained in step i) with acetic anhydride to prepare N-(1, 3-dioxo-1, 3-dihydro-2-benzofuran-4-yl) acetamide (Formula-IV); and iii. condensation of (1S)-1-(3-ethoxy-4-methoxy-phenyl)-2-methanesulfonyl-ethylamine (Formula-V) and N-(1, 3-dioxo-1, 3dihyro-2-benzofuran-4-yl) acetamide (Formula-IV) in presence of methyl isobutyl ketone and acetic acid mixture, wherein MIBK and acetic acid is in the ratio of 11:4 to 12:4.5 to prepare Apremilast (Formula I) having less than 0.15% w/w by HPLC of Des-acetyl impurity.

3. The process as claimed in claim 1 wherein in step i, the reducing agent is 10% Palladium on carbon, or Raney nickel, and the hydrogenation is carried out at temperature range of 5° C. to 25° C.

4. The process as claimed in claim 1 wherein the Cyclization and acetylation of 3-aminobenzene-1, 2-dicarboxylic acid is carried out at temperature range of 90° C. to 140° C.

5. The process as claimed in claim 1, wherein suitable solvent for crystallization in step iv is selected from acetone, ethanol and mixture thereof.

6. A process of hydrogenation of 3-nitrobenzene-1, 2-dicarboxylic acid (Formula - II) to prepare 3-aminobenzene-1, 2-dicarboxylic acid (Formula -III) in the presence of catalyst using Acetone as a solvent.

7. The process as claimed in claim 6, wherein the catalyst is selected from 10% Palladium on carbon and Raney Nickel.

8. The process as claimed in claim 2 wherein in step i, the catalyst is 10% Palladium on carbon or Raney nickel, and the hydrogenation is carried out at temperature range of 5° C. to 25° C.

9. The process as claimed in claim 2 wherein the Cyclization and acetylation of 3-aminobenzene-1, 2-dicarboxylic acid is carried out at a temperature range of 90° C. to 140° C.

* * * * *